United States Patent
Hosseini et al.

(10) Patent No.: US 12,070,442 B2
(45) Date of Patent: *Aug. 27, 2024

(54) OPHTHALMIC PHARMACEUTICAL COMPOSITIONS AND METHODS FOR TREATING OCULAR SURFACE DISEASE

(71) Applicant: SURFACE OPHTHALMICS, INC., Pleasanton, CA (US)

(72) Inventors: Kamran Hosseini, Pleasanton, CA (US); Dennis Elias Saadeh, Irvine, CA (US); Richard L. Lindstrom, Pleasanton, CA (US)

(73) Assignee: SURFACE OPHTHALMICS, INC., Pleasanton, CA (US)

( * ) Notice: Subject to any disclaimer, the term of this patent is extended or adjusted under 35 U.S.C. 154(b) by 589 days.

This patent is subject to a terminal disclaimer.

(21) Appl. No.: 17/418,813

(22) PCT Filed: Dec. 4, 2019

(86) PCT No.: PCT/US2019/064371
§ 371 (c)(1),
(2) Date: Jun. 26, 2021

(87) PCT Pub. No.: WO2020/139525
PCT Pub. Date: Jul. 2, 2020

(65) Prior Publication Data
US 2022/0071945 A1    Mar. 10, 2022

Related U.S. Application Data

(60) Provisional application No. 62/785,312, filed on Dec. 27, 2018.

(51) Int. Cl.
| | | |
|---|---|---|
| *A61K 31/343* | (2006.01) | |
| *A61K 9/00* | (2006.01) | |
| *A61K 9/08* | (2006.01) | |
| *A61K 31/573* | (2006.01) | |
| *A61K 45/06* | (2006.01) | |

(52) U.S. Cl.
CPC .......... *A61K 31/343* (2013.01); *A61K 31/573* (2013.01); *A61K 45/06* (2013.01); *A61K 9/0019* (2013.01); *A61K 9/0048* (2013.01); *A61K 9/08* (2013.01)

(58) Field of Classification Search
None
See application file for complete search history.

(56) References Cited

U.S. PATENT DOCUMENTS

| | | |
|---|---|---|
| 5,514,686 A | 5/1996 | Mochizuki et al. |
| 5,518,732 A | 5/1996 | Nigam |
| 6,489,335 B2 | 2/2002 | Peyman |
| 6,579,901 B2 | 6/2003 | Chen et al. |
| 6,878,694 B2 | 4/2005 | Doshi et al. |
| 7,083,803 B2 | 8/2006 | Peyman |
| 7,087,237 B2 | 8/2006 | Peyman |
| 7,335,682 B2 | 2/2008 | Chen et al. |
| 8,574,562 B2 | 11/2013 | Goebel |
| 9,034,843 B2 | 5/2015 | Matsumura et al. |
| 9,233,123 B1 | 1/2016 | Lindstrom |
| 9,549,966 B2 | 1/2017 | Hamrah et al. |
| 9,572,800 B2 * | 2/2017 | Zarnitsyn ................. A61K 9/10 |
| 9,789,080 B2 | 10/2017 | Hou et al. |
| 10,058,616 B2 | 8/2018 | Hong et al. |
| 10,201,548 B2 | 2/2019 | Bowman et al. |
| 10,206,944 B2 | 2/2019 | De Rosa et al. |
| 10,420,796 B2 | 9/2019 | Funayama et al. |
| 10,507,230 B2 | 12/2019 | Yamamoto et al. |
| 10,555,947 B2 | 2/2020 | Musunuri et al. |
| 10,588,913 B2 | 3/2020 | Tada et al. |
| 10,716,804 B2 | 7/2020 | Funayama |
| 11,207,345 B2 | 12/2021 | Funayama et al. |
| 11,766,421 B2 | 9/2023 | Saadeh et al. |
| 2001/0041671 A1 | 11/2001 | Napoli |
| 2003/0130301 A1 | 7/2003 | Ueno |
| 2005/0063996 A1 | 3/2005 | Peyman |
| 2006/0110459 A1 | 5/2006 | Jafari et al. |
| 2006/0148686 A1 * | 7/2006 | Xia ...................... A61K 9/0048 514/171 |
| 2007/0082841 A1 | 4/2007 | Higuchi et al. |
| 2007/0259021 A1 | 11/2007 | Friedlaender et al. |

(Continued)

FOREIGN PATENT DOCUMENTS

| | | |
|---|---|---|
| EP | 0063973 B1 | 3/1984 |
| EP | 0167363 B1 | 8/1990 |

(Continued)

OTHER PUBLICATIONS

Drugs.com, Mycophenolate, internet article, https://web.archive.org/web/20170511145913/https://www.drugs.com/monograph/mycophenolate.html, 2017. (Year: 2017).*

(Continued)

*Primary Examiner* — Layla D Berry

(74) *Attorney, Agent, or Firm* — Wagenknecht IP Law Group PC

(57) ABSTRACT

Pharmaceutical compositions are described, the compositions comprising an immunosuppressant (such as mycophenolic acid) in combination with a very low concentration of a corticosteroid (such as betamethasone) that are capable of treating, preventing, and/or alleviating an ocular surface disease. Methods for fabricating the compositions and using them are also described.

23 Claims, No Drawings

(56) References Cited

U.S. PATENT DOCUMENTS

| | | |
|---|---|---|
| 2007/0280924 A1 | 12/2007 | Daniels et al. |
| 2008/0242646 A1 | 10/2008 | Lessem et al. |
| 2010/0010082 A1 | 1/2010 | Chong et al. |
| 2010/0286065 A1 | 11/2010 | Lambert et al. |
| 2014/0031298 A1 | 1/2014 | Hughes et al. |
| 2017/0065552 A1* | 3/2017 | Hou .................. A61K 31/722 |
| 2017/0161438 A1 | 6/2017 | Connery et al. |
| 2018/0117064 A1 | 5/2018 | Tada et al. |
| 2018/0333414 A1* | 11/2018 | Musunuri ............ A61K 9/1075 |
| 2019/0008920 A1 | 1/2019 | Arumugham et al. |
| 2019/0298738 A1 | 10/2019 | Bowman et al. |
| 2019/0332516 A1 | 10/2019 | Bowman et al. |
| 2020/0129526 A1 | 4/2020 | Tada et al. |
| 2020/0171075 A1 | 6/2020 | Friedman |
| 2022/0071945 A1 | 3/2022 | Hosseini et al. |
| 2022/0143075 A1 | 5/2022 | Saadeh et al. |
| 2023/0277557 A1 | 9/2023 | Sternberg et al. |

FOREIGN PATENT DOCUMENTS

| | | |
|---|---|---|
| EP | 0232377 B1 | 9/1990 |
| EP | 0517972 B1 | 11/1995 |
| EP | 1188434 B1 | 5/2006 |
| EP | 2560616 B1 | 4/2011 |
| EP | 1948131 B3 | 3/2013 |
| EP | 2946782 B1 | 3/2013 |
| EP | 2937088 B1 | 12/2013 |
| EP | 1173177 B2 | 3/2014 |
| EP | 2979689 A1 | 2/2016 |
| EP | 2493942 B1 | 6/2016 |
| EP | 3409292 B1 | 12/2018 |
| EP | 4088757 A1 | 2/2021 |
| EP | 2695621 B1 | 3/2021 |
| EP | 3023108 B1 | 4/2021 |
| EP | 3831394 A1 | 6/2021 |
| JP | 2009-86619 A | 4/2009 |
| JP | 2016-188237 A | 11/2016 |
| JP | 2017-206547 A | 11/2017 |
| JP | 2018-83805 A | 5/2018 |
| JP | 2018-203792 A | 12/2018 |
| JP | 2019-182825 A | 10/2019 |
| JP | 2019-199469 A | 11/2019 |
| JP | 2020-138928 A | 9/2020 |
| JP | 2021-75531 A | 5/2021 |
| JP | 2022-157707 A | 10/2022 |
| WO | 96/25145 A1 | 8/1996 |
| WO | 2006/073786 A2 | 7/2004 |
| WO | 2005030205 A1 | 4/2005 |
| WO | 2006044155 A2 | 4/2006 |
| WO | 2007092620 A2 | 8/2007 |
| WO | 2018114557 A1 | 6/2018 |
| WO | 2019/060696 A1 | 3/2019 |
| WO | 2017040099 A1 | 3/2019 |
| WO | 2019/216381 A1 | 11/2019 |
| WO | 2020/106337 A1 | 5/2020 |
| WO | 2020/139525 A1 | 7/2020 |
| WO | 2022/240589 A1 | 11/2022 |
| WO | 2023/141334 A2 | 7/2023 |

OTHER PUBLICATIONS

Vichyanond et al. "Use of Cyclosporine A and Tacrolimus in Treatment of Vernal Keratoconjunctivitis" Curr Allergy Asthma Rep, (2013) 13:308-314.

Bhatti et al. "Severe acute fibrinous and organzing pneumonia (AFOP) causing ventilatory failure: Successful treatment with mycophenolate mofetil and corticosteroids", Respiratory Medicine (2009) 13:1764-1767.

Dogru et al., "Pharmacotherapy of dry eye", Epert Opin. Pharmacother. (2011)12(3):325-334.

Gipson et al., "Clinical trial of focal segmental glomerulosclerosis in children and young adults", Kidney International (2011) 80:868-878.

Gumus et al., "The role of inflammation and antiinflammation therapies in keratoconjunctivitis sica", Clinical Ophthamology (2009) 3:57-67.

Vickers et al., "The Future of Dry Eye Treatment: A Glance into the Therapeutic Pipeline", Ophthalmol Ther (2015) 4:69-78.

Matossian et al., Dry Eye Treatment with Topical Cyclosporine 0.1% in Chondroitin Sulfate Opthalmic Emulsion, Clinical Opthalmology (2021)15:1979-1984.

\* cited by examiner

OPHTHALMIC PHARMACEUTICAL COMPOSITIONS AND METHODS FOR TREATING OCULAR SURFACE DISEASE

CROSS REFERENCE TO RELATED APPLICATION(S)

This application is a US national phase application under 35 U.S.C. $371 of international application no. PCT/EP2019/064371, filed Dec. 4, 2019, which claims the benefit of priority under 35 U.S.C. § 119(e) of U.S. provisional patent application no. 62/785,312, filed Dec. 27, 2018, the entire content of each is incorporated herein by reference.

FIELD OF THE INVENTION

The present invention relates generally to the field of ophthalmology and more specifically to compositions and methods for treating, mitigating, and/or preventing ocular surface disease, such as dry eye syndrome in mammals, and to methods of preparing such compositions.

BACKGROUND

An ocular surface disease, such as dry eye syndrome, is an ophthalmic condition that manifests itself in symptoms of discomfort and visual disturbance as a result of decreased tear production, and is characterized by a dysfunction of one or more components of the tear film, the latter being stable in the absence of this disease. Tear deficiency may be caused by poor production of tears as a result of age, hormonal changes, various autoimmune diseases, and other factors, and may also be a side effect of certain medications, such as beta-blockers, antidepressants, antihistamines, etc. However, normal stable condition of the tear film resulting in normal tear secretion is important for the lubrication and maintenance of the refractive surface of the eye.

An ocular surface disease may afflict an individual and vision may be substantially impaired with varying degrees of severity, ranging from burning sensation, a feeling of dryness and persistent irritation up to substantial impairment of vision in more severe cases. Therefore, a variety of approaches have been developed for treatment and therapy of such diseases. Typically, the majority of patients with an ocular surface disease are prescribed or recommended artificial tears. Other methods and devices that are also often recommended include scrubs, drops, inserts, plugs or lid compresses. These products typically include immunologic agents, autologous compounded serum, mucin producing agents and/or lubricants. While some such remedies do exist, and may provide some relief in some cases, in many other instances they are insufficient or too expensive. Accordingly, it is desirable to have better alternative compositions.

This patent specification discloses such pharmaceutical compositions suitable for use in treatment, prevention, and/or alleviation of an ocular surface disease that can achieve positive patient outcomes while being free of drawbacks and deficiencies of existing formulations, and methods of fabricating and administering the same.

SUMMARY

The present disclosure is based on the finding that addition of a very low concentration of a corticosteroid (e.g., betamethasone) to an immunosuppressant, such as mycophenolic acid, provides superior and/or synergistic efficacy for treating, preventing, and/or alleviating an ocular surface disease, such as, but not limited to, keratoconjunctivitis sicca, episodic dry eye disease, recalcitrant dry eye disease, age-related dry eye, neurotrophic ocular surface disease, meibomian gland disease and blepharitis. Accordingly, the invention provides a pharmaceutical composition, the composition including a first component comprising a combination of (i) mycophenolic acid or a pharmaceutically acceptable salt, derivative or analog thereof, and (ii) a corticosteroid or a pharmaceutically acceptable salt, derivative or analogs thereof, wherein the corticosteroid is present at a concentration of about 0.005% w/w to 0.05% w/w, and a carrier selected from the group consisting of de-ionized water and a balanced salt solution.

In various embodiments, the composition may further include at least one second component selected from the group consisting of glycerol, polyvinylpyrrolidone, sorbitol, polyethylene glycol, hydroxypropyl methylcellulose, carboxymethylcellulose, and polyvinyl acetate. In various embodiments, the composition may further include at least one third component selected from the group consisting of a glycosaminoglycan, chondroitin, chondroitin sulfate, dermatan sulfate, dermatin sulfate, heparin sulfate, heparan sulfate, keratin sulfate, keratan sulfate, and hyaluronic acid. In various embodiments, the composition may further include at least one fourth component selected from the group consisting of dextran, dextran sulfate, sodium chloride, dextrose, and sucrose. In various embodiments, the composition may further include at least one additional compound selected from the group consisting of tacrolimus, lifitegrast, cyclosporine, a corticosteroid other than betamethasone, any pharmaceutically acceptable salts, hydrates, solvates, esters thereof or derivatives or analogs thereof, albumin, plasma, platelet-rich plasma, and serum. In various embodiments, the composition may further include at least one antioxidant selected from the group consisting of ascorbic acid, erythorbic acid, sodium ascorbate, thioglycerol, cysteine, acetylcysteine, cystine, dithioerythreitol, dithiothreitol, glutathione, tocopherols, butylated hydroxyanisol, butylated hydroxytoluene, sodium sulfate, sodium bisulfite, acetone sodium bisulfite, sodium metabisulfite, sodium sulfite, sodium formaldehyde sulfoxylate, sodium thiosulfate, and nordihydroguaiaretic acid. In various embodiments, the composition may further include at least one excipient or surfactant selected from the group consisting of a non-ionic polyoxyethlene-polyoxypropylene block copolymer, methylcellulose, a hydroxypropyl methylcellulose polymer, a polycarbophil polymer, edetate disodium dihydrate (EDTA), polysorbate-80, sodium thiosulfate, sodium thiosulfate pentahydrate, sodium phosphate, sodium phosphate dibasic anhydrous, and sodium phosphate monobasic anhydrous.

In various embodiments, the corticosteroid is cyclosporine and the composition further includes (i) at least one second component selected from the group consisting of glycerol, polyvinylpyrrolidone, sorbitol, polyethylene glycol, hydroxypropyl methylcellulose, carboxymethylcellulose, and polyvinyl acetate; (ii) at least one third component selected from the group consisting of a glycosaminoglycan, chondroitin, chondroitin sulfate, dermatan sulfate, dermatin sulfate, heparin sulfate, heparan sulfate, keratin sulfate, keratan sulfate, and hyaluronic acid; and (iii) at least one excipient or surfactant selected from the group consisting of a non-ionic polyoxyethlene-polyoxypropylene block copolymer, methylcellulose, a hydroxypropyl methylcellulose polymer, a polycarbophil polymer, edetate disodium dihydrate (EDTA), polysorbate-80, sodium thiosulfate, sodium thiosulfate pentahydrate, sodium phosphate, sodium phosphate dibasic anhydrous, and sodium phosphate monobasic anhydrous.

In various embodiments, the pharmaceutically acceptable salt of mycophenolic acid is mycophenolate sodium, the corticosteroid is loteprednol etabonate, and the composition further includes (i) at least one second component selected from the group consisting of glycerol, polyvinylpyrrolidone, sorbitol, polyethylene glycol, hydroxypropyl methylcellulose, carboxymethylcellulose, and polyvinyl acetate; (ii) at least one third component selected from the group consisting of a glycosaminoglycan, chondroitin, chondroitin sulfate, dermatan sulfate, dermatin sulfate, heparin sulfate, heparan sulfate, keratin sulfate, keratan sulfate, and hyaluronic acid; and (iii) at least one excipient or surfactant selected from the group consisting of a non-ionic polyoxyethlene-polyoxypropylene block copolymer, methylcellulose, a hydroxypropyl methylcellulose polymer, a polycarbophil polymer, edetate disodium dihydrate (EDTA), polysorbate-80, sodium thiosulfate, sodium thiosulfate pentahydrate, sodium phosphate, sodium phosphate dibasic anhydrous, and sodium phosphate monobasic anhydrous.

In various embodiments, the composition includes mycophenolate sodium and betamethasone sodium phosphate, and the composition further includes (i) at least one second component selected from the group consisting of glycerol, polyvinyl pyrrolidone, sorbitol, polyethylene glycol, hydroxypropyl methylcellulose, carboxymethylcellulose, and polyvinyl acetate; (ii) at least one third component selected from the group consisting of a glycosaminoglycan, chondroitin, chondroitin sulfate, dermatan sulfate, dermatin sulfate, heparin sulfate, heparan sulfate, keratin sulfate, keratan sulfate, and hyaluronic acid; (iii) at least one fourth component selected from the group consisting of dextran, dextran sulfate, sodium chloride, dextrose, and sucrose; and (iv) at least one excipient or surfactant selected from the group consisting of a non-ionic polyoxyethlene-polyoxypropylene block copolymer, methylcellulose, a hydroxypropyl methylcellulose polymer, a polycarbophil polymer, edetate disodium dihydrate (EDTA), polysorbate-80, sodium thiosulfate, sodium thiosulfate pentahydrate, sodium phosphate, sodium phosphate dibasic anhydrous, and sodium phosphate monobasic anhydrous.

In various embodiments, the composition includes mycophenolate sodium and tacrolimus monohydrate, and the composition further includes (i) at least one second component selected from the group consisting of glycerol, polyvinylpyrrolidone, sorbitol, polyethylene glycol, hydroxypropyl methylcellulose, carboxymethylcellulose, and polyvinyl acetate; (ii) at least one third component selected from the group consisting of a glycosaminoglycan, chondroitin, chondroitin sulfate, dermatan sulfate, dermatin sulfate, heparin sulfate, heparan sulfate, keratin sulfate, keratan sulfate, and hyaluronic acid; (iii) at least one fourth component selected from the group consisting of dextran, dextran sulfate, sodium chloride, dextrose, and sucrose; (iv) at least one antioxidant selected from the group consisting of ascorbic acid, erythorbic acid, sodium ascorbate, thioglycerol, cysteine, acetylcysteine, cystine, dithioerythreitol, dithiothreitol, glutathione, tocopherols, butylated hydroxyanisol, butylated hydroxytoluene, sodium sulfate, sodium bisulfite, acetone sodium bisulfite, sodium metabisulfite, sodium sulfite, sodium formaldehyde sulfoxylate, sodium thiosulfate, and nordihydroguaiaretic acid; and (v) at least one excipient or surfactant selected from the group consisting of a non-ionic polyoxyethlene-polyoxypropylene block copolymer, methylcellulose, a hydroxypropyl methylcellulose polymer, a polycarbophil polymer, edetate disodium dihydrate (EDTA), polysorbate-80, sodium thiosulfate, sodium thiosulfate pentahydrate, sodium phosphate, sodium phosphate dibasic anhydrous, and sodium phosphate monobasic anhydrous.

In another aspect, the invention provides methods for using the above-mentioned compositions for treating, preventing, and/or alleviating various forms of an ocular surface disease such as keratoconjunctivitis sicca, episodic dry eye disease, recalcitrant dry eye disease, age-related dry eye, neurotrophic ocular surface disease, meibomian gland disease and blepharitis.

DETAILED DESCRIPTION

A. Terms and Definitions

Unless specific definitions are provided, the nomenclatures utilized in connection with, and the laboratory procedures and techniques of analytical chemistry, synthetic organic and inorganic chemistry described herein, are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, formulating compositions and testing them. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. The section headings used herein are for organizational purposes only and are not to be construed as limiting the subject matter described.

As used herein, "or" means "and/or" unless stated otherwise. Furthermore, use of the term "including" as well as other forms, such as "includes," and "included," is not limiting. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

"About" as used herein means that a number referred to as "about" comprises the recited number plus or minus 1-10% of that recited number. For example, "about" 100 degrees can mean 95-105 degrees or as few as 99-101 degrees, depending on the context. Whenever it appears herein, a numerical range such as "1 to 20" or "1-20" refers to each integer in the given range; i.e., meaning only 1, only 2, only 3, etc., up to and including only 20.

The term "salt" refers to an ionic compound which is a product of the neutralization reaction of an acid and a base.

The terms "solvate" and "hydrate" are used herein to indicate that a compound or a substance is physically or chemically associated with a solvent for "solvates" such as water (for "hydrates").

The term "mycophenolic acid" or "MPA" refers to the compound having the IUPAC name 6-(4-hydroxy-6-methoxy-7-methyl-3-oxo-1H-2-benzofuran-5-yl)-4-methyl-hex-4-enoic acid and the following chemical structure:

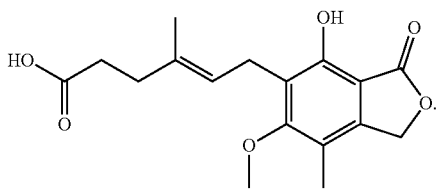 [SMILES: COc1c(C)c2c(c(O)c1C/C=C(\C)CCC(=O)O)C(=O)OC2]

The term "cyclosporine" refers to the compound having the IUPAC name (3S,6S,9S,12R,15S,18S,21S,24S,30S,33S)-30-ethyl-33-[(E,1R,2R)-1-hydroxy-2-methylhex-4-enyl]-1,4,7,10,12,15,19,25,28-nonamethyl-6,9,18,24-tetrakis(2-methylpropyl)-3,21-di(propan-2-yl)-1,4,7,10,13,16,19,22,25,28,31-undecazacyclotritriacontane-2,5,8,11,14,17,20,23,26,29,32-undecone and the following chemical structure:

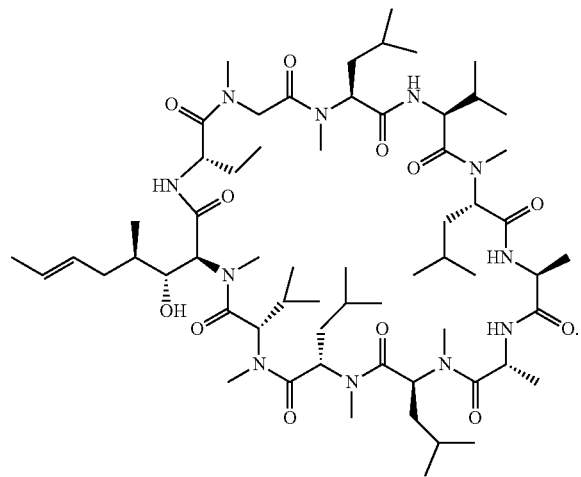 [SMILES: C/C=C/C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

The term "corticosteroid" refers to any steroid hormone, both produced synthetically and obtained from the adrenal cortex of vertebrates (inclusive of both glucocorticoids and mineralocorticoids) and belonging to a sub-genus of steroids that are derivatives of corticosterone, the latter having the chemical structure:

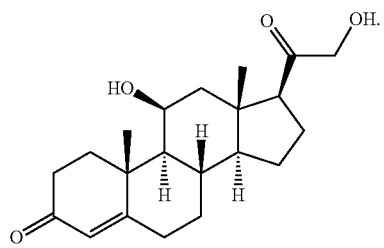

The term "tacrolimus," also known as fujimycin or FK506, refers to an compound having the IUPAC name (−)-(3S,4R,5S,8R,9E,12S,14S,15R,16S 18R,26aS)-8-allyl-5,6,8,11,12,13,14,15,16,17,18,19,24,25,26,26a-hexadeca-hydro-5,19-dihydroxy-3-{(E)-2-[(1R,3R,4R)-4-hydroxy-3-methylcyclohexyl]-1-methylvinyl}-14,16-dimethoxy-4,10,12,18-tetramethyl-15,19-epoxy-3H-pyrido[2,1-c][1,4]oxaazacyclotricosane-1,7,20,21(4H,23H)-tetrone, and the following chemical structure:

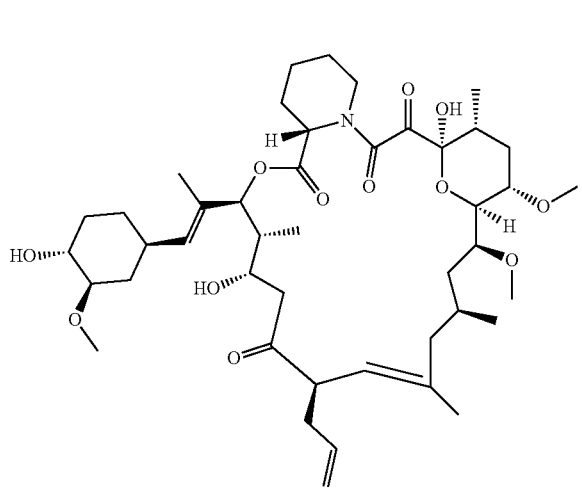 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

The term "albumin" refers to any not glycosylated proteins found in blood plasma.

The term "plasma" refers to blood plasma, i.e., a liquid that comprises extracellular matrix of blood cells.

The term "platelet-rich plasma" refers to a concentrate derived from blood, from which red blood cells have been removed.

The term "serum" refers to a protein-rich liquid obtained in the process of coagulation of blood, i.e., plasma from which clotting proteins have been removed.

The term "glycosaminoglycan" refers to any unbranched polysaccharide comprising a repeating disaccharide unit.

The term "deturgescent agent" refers to a compound that is capable of maintaining the stroma of the cornea of the eye in a state of relative dehydration to an extent necessary to ensure the transparency of the cornea.

In various embodiments of the invention, the acceptable surfactant or solubilizing and suspending agent may be any of non-ionic polyoxyethlene-polyoxypropylene block copolymers, optionally partially cross-linked polyacrylates, polyoxyethylene sorbitan monolaurates, polyoxyethylene sorbitan monopalmitates, polyoxyethylene sorbitan monostearates, polyoxyethylene sorbitan monooleates, glyceryl distearate, triglycerol monooleate, and combinations thereof.

The term "ocular surface disease" (including "dry eye" or "dry eye syndrome") is defined as one or several conditions associated with, or caused by, either decreased or insufficient tear production or increased or excessive tear film evaporation, or both, and characterized by redness, itching, and burning of the eye. An ocular surface disease is further defined as being inclusive of keratoconjunctivitis sicca, episodic dry eye disease, recalcitrant dry eye disease, age-related dry eye, neurotrophic ocular surface disease, meibomian gland disease and blepharitis.

The term "pharmaceutical composition" is defined as a chemical or a biological compound or substance, or a mixture or combination of two or more such compounds or substances, intended for use in the medical diagnosis, cure, treatment, or prevention of disease or pathology.

The term "therapeutically effective amount" is defined as the amount of the compound or pharmaceutical composition that will elicit the biological or medical response of a tissue, system, animal or human that is being sought by the researcher, medical doctor or other clinician. Thus, the term "therapeutically effective amount" is used herein to denote any amount of a formulation that causes a substantial improvement in a disease condition when applied to the affected areas repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

The term "pharmaceutically acceptable," when used in the context of a carrier, is defined as a carrier, whether diluent or excipient, that is compatible with the other ingredients of the formulation and not deleterious to the recipient thereof.

The terms "administration of a composition" or "administering a composition" are defined to include an act of providing a compound or pharmaceutical composition of the invention to the subject in need of treatment.

The term "subject," as used herein, refers to any individual or patient to which the subject methods are performed. Generally, the subject is human, although as will be appreciated by those in the art, the subject may be an animal.

As used herein, "treatment" or "treating" means to administer a composition to a subject or a system with an undesired condition. The condition can include a disease or disorder. "Prevention" or "preventing" means to administer a composition to a subject or a system at risk for the condition. The condition can include a predisposition to a disease or disorder. The effect of the administration of the composition to the subject (either treating and/or preventing) can be, but is not limited to, the cessation of one or more symptoms of the condition, a reduction or prevention of one or more symptoms of the condition, a reduction in the severity of the condition, the complete ablation of the condition, a stabilization or delay of the development or progression of a particular event or characteristic, or minimization of the chances that a particular event or characteristic will occur.

B. Embodiments of the Invention

As topical corticosteroids are included in treatment guidelines and are widely used for the treatment for dry eye disease, the addition of a very low concentration of a corticosteroid (e.g., betamethasone) to an immunosuppressant, such as mycophenolic acid, is expected to provide superior and/or synergistic efficacy compared to standard treatment protocols. In consideration of the very low concentration of corticosteroid incorporated into such treatments, no negative impact on safety is anticipated. It is also anticipated that such compositions will ultimately lead to steroid sparing effects, as demonstrated with oral CELL-CEPT® monotherapy accepted for use in the treatment of inflammatory eye disease.

Accordingly, the pharmaceutical compositions provided herein may be used to treat, prevent, and/or alleviate an ocular surface disease, such as, but not limited to, keratoconjunctivitis sicca, episodic dry eye disease, recalcitrant dry eye disease, age-related dry eye, neurotrophic ocular surface disease, meibomian gland disease and blepharitis.

Likewise, the pharmaceutical compositions may be useful for preventative and therapeutic treatment of other ophthalmic conditions and diseases as they are expected to provide numerous medical benefits such as for ocular surface (e.g., cornea and conjunctiva) lubrication, corneal deturgescence, cell membrane stabilization, etc. The compositions of the present invention are therefore expected to bring about significant relief to sufferers of such diseases.

Among other benefits, there is expected no uncomfortable "stinging" feeling in the eye (i.e., no burning sensation) after the composition has been topically administered. As such, the pharmaceutical compositions provided herein may also be useful for protecting the ocular surface, corneal epithelial cells, corneal endothelial cells, and/or other ocular tissues during an eye surgery; may be useful for wound healing after various injuries to the eye; may be useful for reducing corneal edema (e.g., during and after corneal transplantation surgery); and/or may be useful for rehabilitating the ocular surface before and/or after contact lens wear, etc.

In various embodiments, the pharmaceutical compositions include a first component that comprises, consists of, or consists essentially of, a combination of an immunosuppressant drug and about 0.005% w/w to about 0.05% w/w of a corticosteroid. In various embodiments, the amount of the corticosteroid in the first component may be between about 0.008% w/w to about 0.05% w/w, between about 0.009% w/w to about 0.05% w/w, between about 0.01% w/w to about 0.04% w/w, or preferably, between about 0.02% w/w and about 0.04% w/w. In various embodiments, the amount of the corticosteroid in the first component is about 0.03% w/w.

In various embodiments, the first component may include an immunosuppressant drug in a mass concentration range of between about 0.05% w/w to about 1.0% w/w, such as between about 0.08% w/w to about 0.8% w/w, between about 0.1% w/w to about 0.6% w/w, between about 0.2% w/w to about 0.5% w/w, or preferably, between about 0.25% w/w and about 0.4% w/w. In various embodiments, the about of immunosuppressant drug is about 0.3% w/w.

The compositions may further include a carrier such as de-ionized water and/or balanced salt solution. In various embodiments, the balanced salt solution used in the compositions of the invention include: potassium chloride, calcium chloride, magnesium chloride, sodium chloride, sodium acetate and sodium citrate. Thus, the total contents of the first component in the composition (regardless of the number of drugs in the first component) may be between about 0.001% w/w and about 75.0% w/w, such as between about 0.01 w/w and about 50% w/w, between about 0.1% w/w and about 50% w/w, between about 0.2% w/w and about 25.0% w/w, between about 0.25% w/w and about 1.0% w/w, or preferably, between about 0.25% w/w and about 0.5% w/w.

Exemplary immunosuppressant drugs useful in the first component of the pharmaceutical compositions provided herein include, but are not limited to, mycophenolic acid, tacrolimus, cyclosporine, or any pharmaceutically acceptable salt or derivative thereof. In various embodiments, the immunosuppressant drug is mycophenolic acid, which may be present in a solution or suspension either as a part of a polycarbophil-based formulation or as a part of a non-polycarbophil-based formulation. Exemplary salts of mycophenolic acid useful in the compositions of the invention include, but are not limited to, mycophenolate sodium, and mycophenolate mofetil.

Exemplary corticosteroids useful in the first component of the pharmaceutical compositions provided herein include, but are not limited to, betamethasone, loteprednol, loteprednol etabonate, triamcinolone, triamcinolone acetonide, triamcinolone diacetate, triamcinolone benetonide, triamcinolone furetonide, triamcinolone hexacetonide, dexamethasone, fluorometholone, fluocinolone acetonide, prednisone, prednisolone, methylprednisone, corticol, cortisone, fluorocortisone, deoxycorticosterone acetate, aldosterone, and a budesonide. In various embodiments, the immunosuppressant drug is betamethasone, which may be present as a derivative or analog thereof, such as, but not limited to, betamethasone acetate, betamethasone sodium phosphate, betamethasone valerate, and/or betamethasone dipropionate.

Accordingly, in various embodiments, the first component of the composition comprises, consists of, or consists essentially of, a combination of mycophenolic acid and betamethasone, each being provided at the various concentration ranges described above. In various embodiments the first component includes about 0.3% w/w mycophenolic acid and about 0.03% w/w betamethasone, and may optionally include one or more of: tacrolimus, cyclosporine, a corticosteroid other than betamethasone, any pharmaceutically acceptable salts, hydrates, solvates, esters thereof or derivatives or analogs thereof, albumin, plasma, platelet-rich plasma, and serum. In various embodiments, the first component may also include a therapeutically effective amount of lifitegrast (commercially available as XIIDRA®), which has been shown to reduce inflammation by inhibiting inflammatory cell binding and is used for treating dry eye disease.

In those embodiments where the first component comprises an additional corticosteroid other than betamethasone, the corticosteroid that can be employed can be any of loteprednol, loteprednol etabonate, triamcinolone, triamcinolone acetonide, triamcinolone diacetate, triamcinolone benetonide, triamcinolone furetonide, triamcinolone hexacetonide, dexamethasone, fluorometholone, fluocinolone acetonide, prednisone, prednisolone, methylprednisone, corticol, cortisone, fluorocortisone, deoxycorticosterone acetate, aldosterone, a budesonide, or any combination thereof.

A second component that may be included in the pharmaceutical compositions provided herein is a lubricating agent, which may be selected from the group consisting of glycerol, glycerin, or glycerine. Alternatively, or in addition thereto, the lubricating agent may include one or more secondary lubricating agents. Non-limiting examples of acceptable secondary lubricating agent(s) that may be so used include any of: polyvinylpyrrolidone, sorbitol, polyethylene glycol, hydroxypropyl methylcellulose, carboxymethylcellulose, and polyvinyl acetate. In various embodiments, the total content of the second component in the composition (regardless of the total number of lubricating agents used) expressed as the mass concentration may be between about 0.1% w/w and about 5.0% w/w, such as between about 1.0% w/w and about 4.0% w/w, for example, preferably about 1.0% w/w.

A third component that may be included in the pharmaceutical compositions provided herein is at least one glycosaminoglycan. It can be theorized, without firm commitment to any particular or specific mechanism, that glycosaminoglycans may be useful in protecting endothelial and epithelial cells which are subject to exposure to trauma, and/or to promote the growth of such cells. Non-limiting examples of glycosaminoglycan(s) that may be used include: chondroitin, chondroitin sulfate, dermatan sulfate, dermatin sulfate, heparin sulfate, heparan sulfate, keratin sulfate, keratan sulfate, and hyaluronic acid. In various embodiments, the glycosaminoglycan that can be so used is chondroitin sulfate. The total content of the glycosaminoglycan(s) in the composition, when present, expressed as the mass concentration may be between about 0.1% w/w and about 5.0% w/w, such as between about 0.2% w/w and about 4.0% w/w, for example preferably about 0.25% w/w.

A fourth component that may be included in the pharmaceutical compositions provided herein is at least one deturgescent agent. One non-limiting example of an acceptable deturgescent agent that may be so used is dextran sulfate. Non-limiting examples of other acceptable deturgescent agent(s) that may be used in addition to, or instead of, dextran sulfate include any of: dextran, sodium chloride, dextrose, and sucrose. While such deturgescent agents are typically used to provide dehydration for stroma of the cornea of the eye, it has been unexpectedly found that inclusion of at least one deturgescent agent may be beneficial for improving outcomes in the treatment of various surface ocular diseases such as dry eye syndromes. The total content of the deturgescent agent(s) in the composition expressed as the mass concentration may be between about 0.1% w/w and about 5.0% w/w, such as between about 0.2% w/w and about 4.0% w/w, for example preferably about 0.25% w/w.

In some embodiments, the composition may also include one or more antioxidants selected from the group consisting of ascorbic acid derivatives such as ascorbic acid, erythorbic acid, and sodium ascorbate; thiol derivatives such as thioglycerol, cysteine, acetylcysteine, cystine, dithioerythreitol, dithiothreitol, glutathione; tocopherols; butylated hydroxyanisol (BHA); butylated hydroxytoluene (BHT); sulfurous acid salts such as sodium sulfate, sodium bisulfite, acetone sodium bisulfite, sodium metabisulfite, sodium sulfite, sodium formaldehyde sulfoxylate, and sodium thiosulfate; and nordihydroguaiaretic acid.

As mentioned above, in addition to the above-described components, the compositions also include a carrier. In various embodiments, the carrier is pure de-ionized water and may further include a balanced salt solution, as is known to those having ordinary skill in the art. In yet other embodiments, the carrier may, in addition to water and/or the balanced salt solution, further optionally contain one or more pharmaceutically acceptable excipient(s) or surfactants. In various embodiments total content of the excipient or surfactant portion in the composition (regardless of the number of excipients or surfactants used) expressed as the mass concentration may be between about 0.1% w/w and about 5.0% w/w, such as between about 0.1% w/w and about 4.0% w/w, between about 0.2% w/w and about 4.0% w/w, between about 0.3% w/w and about 3.0% w/w, between about 0.4% w/w and about 2.0% w/w, or preferably, between about 0.5% w/w and about 1.0% w/w.

In various embodiments, the excipient or surfactant may be a non-ionic polyoxyethlene-polyoxypropylene block copolymer having the following general structure:

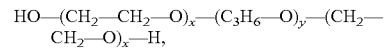

wherein x is an integer having the value of at least 8 and y is an integer having the value of at least 38.

One non-limiting example of a specific non-ionic polyoxyethlene-polyoxypropylene block copolymer that can be used as a excipient or surfactant in the pharmaceutical compositions of the instant invention is the product known under the trade names Poloxamer 407® and PLURONIC® F-127 (poly(ethylene glycol)-block-poly(propylene glycol)-block-poly(ethylene glycol)), with the molecular weight of the polyoxypropylene portion of about 4,000 Daltons, about a 70% polyoxyethylene content, the overall molecular weight of between about 9,840 Daltons and about 14,600 Daltons. Another non-limiting example of a non-ionic poly (oxyethlene-co-oxypropylene) block copolymer that can be used is the product known under the trade name Poloxamer 188 (P188), which has an overall molecular weight of about 8400 Daltons. Each of which have the following chemical structure:

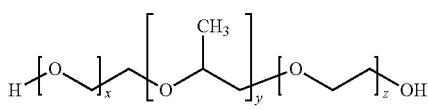

where x and z=80 and y=27 for P188; and where x and z=101 and y=56 for P407.

Another type of product that can be used in the excipient or surfactant portion of the pharmaceutical formulation may be water-soluble methylcellulose and hydroxypropyl methylcellulose polymers, such as METHOCEL® family of products, for example, a hydroxypropyl methylcellulose product METHOCEL® E4M. The compositions may also contain a quantity of preservative(s) such as benzalkonium chloride, if desired.

Yet another type of product that can be used in the excipient or surfactant portion of the pharmaceutical composition may be a polycarbophil polymer product (i.e., a polymeric product based on polyacrylic acid cross-linked with divinyl glycol) which is available under a variety of trade names such as FIBERCON®, EQUALACTIN®, KONSYL FIVER®, etc. If a polycarbophil product is used it may also be present as a part of mycophenolic acid solution, as mentioned above.

Additional exemplary excipients or surfactants that can be used in the pharmaceutical compositions provided herein include, but are not limited to, edetate disodium dihydrate (EDTA), polysorbate-80, sodium thiosulfate, sodium thiosulfate pentahydrate, sodium phosphate, sodium phosphate dibasic anhydrous, and sodium phosphate monobasic anhydrous.

Finally, the ophthalmic compositions will typically have an osmolarity between about 100 and about 500 milliosmoles per liter (mOsm/L), such as between about 150 mOsm/L and about 450 mOsm/L, for example, preferably between about 200 mOsm/L and about 400 mOsm/L. A tonicity modulating agent, such as sodium chloride, may also be used in the compositions.

According to further embodiments, methods for fabricating the above-described pharmaceutical compositions are provided. A one-batch formulation method may be used, where the components of the pharmaceutical formulation can be combined in single container; the components may be added to the container simultaneously or consecutively. Alternatively, a two- or multiple-batch method(s) may be used if desired, where each component of the pharmaceutical formulation can be combined in separate container followed by combining the contents of each container. The resulting product may then be sterilized and transferred into single dose vials, followed by capping and sealing the vials. In various embodiments, the pharmaceutical compositions may be filter sterilized or autoclaved.

Alternatively, when one or more components (e.g., betamethasone) are highly hydroscopic, it may be difficult to accurately weigh forms of those components when preparing the formulation. As such, the methods for fabricating the above-described pharmaceutical compositions may further include preparation of a stock solution of each highly hydroscopic component (e.g., betamethasone) by dissolving a fixed amount of the component (e.g., betamethasone) in a known amount of water and determining the solution concentration by analyzing the content of the component (e.g., betamethasone) by high pressure liquid chromatograph (HPLC). The component (e.g., betamethasone) may then be added to the batch by calculating the amount of stock solution necessary to attain the appropriate concentration thereof and adding the calculated amount of stock solution to the batch.

Accordingly, the methods for fabricating the above-described pharmaceutical compositions may include a one-batch formulation method, where most of the components of the pharmaceutical formulation are combined with one or more of the above-discussed stock solution(s) of hydroscopic components (e.g., betamethasone) in single container, with each component being added to the container simultaneously or consecutively. Alternatively, a two- or multiple-batch method(s) may be used if desired, where each component of the pharmaceutical formulation can be combined in separate containers, including preparation of one or more stock solutions of hydroscopic components (e.g., betamethasone), followed by combining the contents of each container. The resulting product may then be sterilized and transferred into single dose vials, followed by capping and sealing the vials. In various embodiments, the pharmaceutical compositions may be filter sterilized or autoclaved.

As is known in the art, certain pharmaceutical compositions including mycophenolic acid or a salt thereof as an active ingredient in an aqueous medium with a reduced level of dissolved oxygen relative to saturation level were more stable than formulations with aqueous media having saturated levels of dissolved oxygen. Thus, the method of preparing the pharmaceutical compositions described herein may optionally further include a step of removing dissolved oxygen from the formulation. The removal of dissolved oxygen from the composition can be carried out by any conventional means including applying a vacuum to the medium and/or inert atmosphere distillation, freeze-thaw degassing, use of degassing filters, etc., as described in US Pub. No. 2017/006552, incorporated herein by reference. Thus, the process for preparing such compositions can further include packaging the composition in an opaque (e.g., amber) container to prevent exposure of the composition to a substantial amount of light and/or with an inert atmosphere. In various embodiments, the process can include purging the empty container with an inert gas, e.g., $N_2$, before filling and subsequently filling the container with the pharmaceutical composition. The container can be opaque when filled and can be wrapped with a label or metal foil to prevent the formulation from being exposed to substantial light. A container including a metal foil also advantageously reduces oxygen permeability from the atmosphere through the container. The containers can be of the type for a single dose administration; e.g., in a bottle, jar, ampoule, tube, syringe, envelope, container, unit dose container or vial or the container can be of the type that is capable of holding multiple doses; e.g., in resealable glass or plastic eyedropper bottles, etc. The bottles, whether multi-dose or single dose, can be packaged in a laminate pouch including a metal foil to minimize exposer to oxygen from the atmosphere. Further, the pouch can be filled with an inert atmosphere to further reduce oxygen exposure over long-term storage to improve stability. Finally, a complete sterility and endotoxin analysis may be performed on the product according to commonly used methods known to those having ordinary skill in the art.

In various embodiments, the pharmaceutical formulations described herein can be delivered or administered topically, e.g., via eye drops, or may be administered by direct injection into the eye. An ordinarily skilled physician may prescribe delivery by any other acceptable method if so desired and indicated, for example, by ophthalmic gel or ointment.

More specifically, the ophthalmic compositions described hereinabove may be administered as a single dosage, in periodic applications, or may be maintained on the ophthalmic tissue continuously or substantially continuously as appropriate for the particular use. For example, the compositions may be administered once per day, or once every minute for a period of 5 to 10 minutes, or more frequently, or less frequently. To illustrate, an effective amount of the ophthalmic composition may be applied between 1 to 16 times a day (e.g., from 1 to 8 times per day, from 1 to 6 times per day, or from 1 to 4 times per day), or more frequently, or less frequently, as needed.

It will be understood by those having ordinary skill in the art that the specific dose level and frequency of dosage for any particular patient may be varied and will depend upon a variety of factors including the activity of the specific compound employed, the metabolic stability and length of action of that compound, the age, body weight, general health, gender, diet, and the severity of the particular disease or condition being treated.

In additional embodiments, pharmaceutical kits are provided. The kit includes a sealed container approved for the storage of pharmaceutical compositions, the container containing one of the above-described pharmaceutical compositions. An instruction for the use of the composition and the information about the composition are to be included in the kit. Exemplary sealed containers useful in the kits include, but are not limited to, reusable or disposable storage bottles, resealable or disposable foil pouches, etc.

The following examples are provided to further elucidate the advantages and features of the present invention, but are not intended to limit the scope of the invention. The example is for the illustrative purposes only. USP pharmaceutical grade products were used in preparing the formulations described below.

C. Examples

Example 1. Preparing a Pharmaceutical Composition No. 1

A pharmaceutical composition was prepared as described below. The following components were used in the amounts specified:
 (a) about 0.321 g of mycophenolate sodium;
 (b) about 0.05% cyclosporine;
 (c) about 0.25 g of chondroitin sulfate (bovine);
 (d) about 0.10 g of powdered edetate disodium dihydrate;
 (e) about 0.2 g of PLURONIC® F-127;
 (f) about 1.0 mL of glycerol;
 (g) about 0.2% polysorbate-80;
 (h) about 0.125 g of METHOCEL® E4M; and
 (i) about 100 mL of balanced salt solution.

Mycophenolate sodium, chondroitin sulfate, edetate disodium dehydrate, polysorbate-80 and PLURONIC® F-127 were combined with about 90% of the balanced salt solution and stirred until completely dissolved. With continued stirring, METHOCEL® E4M was added followed by addition of glycerol. The pH of the solution was then adjusted to about 6.8-7.2 using sodium hydroxide solution and the remainder of the balanced salt solution was added.

This first step was then filtered through a 0.2 micron filter and placed in an ISO 5 environment with continued stirring. Using aseptic technique, sterile cyclosporine powder was then added to the sterilized solution prepared as described above. The final product was then filled aseptically into pre-sterilized dropper bottles or unit dose vials and sealed.

Example 2. Preparing a Pharmaceutical Composition No. 2

A pharmaceutical composition was prepared as described below. The following components were used in the amounts specified:
 (a) about 0.321 g of mycophenolate sodium powder;
 (b) about 0.2 g of loteprednol etabonate;
 (c) about 0.25 g of chondroitin sulfate (bovine);
 (d) about 0.10 g of powdered edetate disodium dihydrate;
 (e) about 0.2 g of PLURONIC® F-127;
 (f) about 1.0 mL of glycerol;
 (g) about 0.1 g polysorbate-80;
 (h) about 1 g of polyvinylpyrrolidone;
 (i) about 0.125 g of METHOCEL® E4M; and
 (j) about 100 mL of balanced salt solution.

Mycophenolate sodium, chondroitin sulfate, edetate disodium dehydrate, polyvinylpirrolidone, polysorbate-80 and PLURONIC® F-127 were combined with about 90% of the balanced salt solution and stirred until completely dissolved. With continued stirring, METHOCEL® E4M was added followed by addition of glycerol. The pH of the solution was then adjusted to about 5.6 to 5.8 using sodium hydroxide solution and the remainder of the balanced salt solution was added.

The resulting solution was then filtered through a 0.2 micron filter and placed in an ISO 5 environment with continued stirring. Using aseptic technique, sterile loteprednol etabonate powder was then added to the sterilized solution above. The final product was then filled aseptically into pre-sterilized dropper bottles or unit dose vials and sealed.

Example 3. Preparing a Pharmaceutical Composition No. 3

A pharmaceutical composition was prepared as described below. The following components were used in the amounts specified:
 (a) about 0.321 g of mycophenolate sodium powder;
 (b) about 0.01 g of betamethasone sodium phosphate powder;
 (c) about 0.25 g of chondroitin sulfate (bovine);
 (d) about 0.25 of powdered dextran 70,000;
 (e) about 0.30 g of powdered sodium thiosulfate pentahydrate;
 (f) about 0.20 g of PLURONIC® F-127;
 (g) about 1.0 mL of glycerol;
 (h) about 1.17 g of sodium phosphate dibasic anhydrous;
 (i) about 0.4 g of sodium phosphate monobasic anhydrous;
 (j) about 0.10 g of METHOCEL® E4M;
 (k) about 40 mL of balanced salt solution; and
 (l) about 100 mL of sterile injectable water.

Chondroitin sulfate, dextran, sodium thiosulfate, and PLURONIC® F-127 were combined with 90% of the balanced salt solution and about 90% of the water and stirred until completely dissolved followed by addition of glycerol with continued stirring. The pH of the solution was then adjusted to about 7.0 using sodium hydroxide solution before introducing mycophenolate sodium. A stock solution of 1% betamethasone was prepared by dissolving 1 gm of betamethasone sodium phosphate powder in 100 mL water and confirming the stock solution concentration by HPLC. 1 ml of the 1% betamethasone stock solution was then added to the mixture with continued stirring.

With continued stirring, mycophenolate sodium was added slowly followed by addition of METHOCEL® E4M, adjusting pH to about 7.3-7.4, and addition of the remainder of the water. The solution was then filtered through a 0.2 micron filter into sterile dropper bottles or unit dose vials.

Example 4. Preparing a Pharmaceutical Composition No. 4

A pharmaceutical composition was prepared as described below. The following products were used in the amounts specified:
(a) about 0.321 g of mycophenolate sodium powder;
(b) about 0.0255 g of tacrolimus monohydrate powder;
(c) about 0.25 g of chondroitin sulfate (bovine);
(d) about 0.25 of powdered dextran 70,000;
(e) about 0.1 g of edetate disodium powder;
(f) about 0.30 g of powdered sodium thiosulfate pentahydrate;
(g) about 0.20 g of PLURONIC® F-127;
(h) about 1.0 mL polysorbate-80;
(i) about 4.0 mL polyethylene glycol 400 MW;
(j) about 1.0 mL of glycerol;
(k) about 1.17 g of sodium phosphate dibasic anhydrous;
(l) about 0.14 g of sodium phosphate monobasic anhydrous;
(m) about 0.10 g of METHOCEL® E4M;
(n) about 40 mL of balanced salt solution; and
(o) about 100 mL of sterile injectable water.

Chondroitin sulfate, dextran, sodium thiosulfate, and PLURONIC® F-127 were combined with the balanced salt solution and about 90% of the water and stirred until completely dissolved followed by addition of glycerol with continued stirring. The pH of the solution was then adjusted to about 7.0 using sodium hydroxide solution before introducing mycophenolate sodium.

With continued stirring, mycophenolate sodium and tacrolimus monohydrate were added slowly followed by adding METHOCEL® E4M and adjusting pH to about 7.3-7.4 and the remainder of water was added. The solution was then filtered through a 0.2 micron filter into sterile dropper bottles or unit dose vials.

Examples 5-12: Preparing Injectable Pharmaceutical Formulations of Mycophenolic Acid and Betamethasone Sodium Phosphate

| | Example Number | | | | | | | |
|---|---|---|---|---|---|---|---|---|
| Ingredient | 5 | 6 | 7 | 8 w/w % | 9 | 10 | 11 | 12 |
| Mycophenolate Sodium USP[1] | 0.125 | 0.66 | 0.66 | 0.125 | 0.66 | NA | NA | NA |
| Betamethasone Sodium Phosphate, USP | 0.01 | 0.01 | 0.01 | NA | NA | 0.01 | 0.5 | 0.5 |
| Chondroitin Sulfate USP | 0.25 | 0.25 | 0.25 | 0.25 | 0.25 | 0.25 | 0.25 | 0.25 |
| Dextran-40 USP | 0.25 | 0.25 | 0.25 | 0.25 | 0.25 | 0.25 | 0.25 | 0.25 |
| Sodium Thiosulfate USP | 0.3 | 0.3 | 0.3 | 0.3 | 0.3 | 0.3 | 0.3 | 0.3 |
| Edetate Disodium USP | 0.1 | 0.1 | 0.1 | 0.1 | 0.1 | 0.1 | 0.1 | 0.1 |
| Potassium Chloride USP | 0.0225 | 0.0225 | 0.0225 | 0.0225 | 0.0225 | 0.0225 | 0.0225 | 0.0225 |
| Calcium Chloride USP | 0.0144 | 0.0144 | 0.0144 | 0.0144 | 0.0144 | 0.0144 | 0.0144 | 0.0144 |
| Magnesium Chloride Hexahydrate USP | 0.009 | 0.009 | 0.009 | 0.009 | 0.009 | 0.009 | 0.009 | 0.009 |
| Sodium Phosphate Dibasic USP | 0.995 | 0.995 | 0.995 | 0.995 | 0.995 | 0.995 | 0.995 | 0.995 |
| Sodium Phosphate Monobasic USP | 0.204 | 0.204 | 0.204 | 0.204 | 0.204 | 0.204 | 0.204 | 0.204 |
| Poloxamer 407 NF | 0.2 | 0.2 | 0.2 | 0.2 | 0.2 | 0.2 | 0.2 | 0.2 |
| Hypromellose USP (Substitution type 2910) 4000 mPas | 0.2 | 0.2 | 0.2 | 0.2 | 0.2 | 0.2 | 0.2 | 0.2 |
| Glycerin USP | 0.1 | 0.1 | 0.1 | 0.1 | 0.1 | 0.1 | 0.1 | 0.1 |
| Sodium Hydroxide, NF | Q.S. to adjust pH | Q.S. to adjust pH | Q.S. to adjust pH | Q.S. to adjust pH | Q.S. to adjust pH | Q.S. to adjust pH | Q.S. to adjust pH | Q.S. to adjust pH |
| Hydrochloric Acid, NF | Q.S. to adjust pH | Q.S. to adjust pH | Q.S. to adjust pH | Q.S. to adjust pH | Q.S. to adjust pH | Q.S. to adjust pH | Q.S. to adjust pH | Q.S. to adjust pH |
| Sterile Water for Injection, USP | Q.S. to 100% | Q.S. to 100% | Q.S. to 100% | Q.S. to 100% | Q.S. to 100% | Q.S. to 100% | Q.S. to 100% | Q.S. to 100% |

[1]Concentrations listed are for the mycophenolate formulations are adjusted for expression as mycophenolic acid content.
NA = Not added
Q.S. = quantum satis Chondroitin sulfate (depending on formulation), dextran, sodium thiosulfate, sodium chloride, potassium chloride, calcium chloride, magnesium chloride, sodium acetate, sodium phosphates, and poloxamer 407 were combined with about 90% of water and stirred until each component was completely dissolved followed by addition of glycerol with continued stirring. The pH of each solution was then adjusted to about 7.0 using sodium hydroxide solution before introducing mycophenolate sodium and/or betamethasone sodium phosphate.

For example, a stock solution of 2.0% betamethasone was prepared by dissolving 2.0 gm of betamethasone sodium phosphate powder in about 100 mls of water and confirming the stock solution concentration by HPLC. 10 ml of the 2.0% betamethasone stock solution was then added (depending on formulation) to the respective mixtures with continued stirring assuming 100 gm of the final formulation of 0.2% betamethasone.

With continued stirring, mycophenolate sodium and/or betamethasone sodium phosphate (depending on formulation) were added slowly followed by addition of the remainder of water and adjusting pH to about 7.3-7.4. Each solution was then filtered through a 0.2 micron filter into sterilized amber glass injection vials.

Although the invention has been described with the reference to the above examples, it will be understood that modifications and variations are encompassed within the spirit and scope of the invention. Accordingly, the invention is limited only by the following claims.

What is claimed is:

1. A pharmaceutical composition comprising:
   (a) a first component comprising a combination of (i) mycophenolic acid or a pharmaceutically acceptable salt thereof at a concentration of 0.05% w/w to 1.0% w/w, and (ii) betamethasone or a pharmaceutically acceptable salt thereof at a concentration of about 0.005% w/w to 0.05% w/w; and
   (b) a pharmaceutically acceptable carrier.

2. The pharmaceutical composition of claim 1, wherein the pharmaceutically acceptable salt of mycophenolic acid is mycophenolate sodium.

3. The pharmaceutical composition of claim 1, wherein the pharmaceutically acceptable salt of betamethasone is betamethasone sodium phosphate.

4. The pharmaceutical composition of claim 1, further comprising at least one second component selected from the group consisting of glycerol, polyvinylpyrrolidone, sorbitol, polyethylene glycol, hydroxypropyl methylcellulose, carboxymethylcellulose, and polyvinyl acetate.

5. The pharmaceutical composition of claim 4, wherein the concentration of the second component is between about 0.1% w/w and about 5.0% w/w.

6. The pharmaceutical composition of claim 4, further comprising at least one third component selected from the group consisting of a glycosaminoglycan, chondroitin, chondroitin sulfate, dermatan sulfate, dermatin sulfate, heparin sulfate, heparan sulfate, keratin sulfate, keratan sulfate, and hyaluronic acid.

7. The pharmaceutical composition of claim 6, wherein the concentration of the third component is between about 0.1% w/w and about 5.0% w/w.

8. The pharmaceutical composition of claim 6, further comprising at least one fourth component selected from the group consisting of dextran, dextran sulfate, sodium chloride, dextrose, and sucrose.

9. The pharmaceutical composition of claim 8, wherein the concentration of the fourth component is between about 0.1% w/w and about 5.0% w/w.

10. The pharmaceutical composition of claim 1, further comprising at least one additional compound selected from the group consisting of tacrolimus, lifitegrast, cyclosporine, a corticosteroid other than betamethasone, pharmaceutically acceptable salts, derivatives or analogs thereof, albumin, plasma, platelet-rich plasma, and serum.

11. The pharmaceutical composition of claim 10, wherein the corticosteroid other than betamethasone is selected from the group consisting of loteprednol, triamcinolone, triamcinolone acetonide, triamcinolone diacetate, triamcinolone benetonide, triamcinolone furetonide, triamcinolone hexacetonide, dexamethasone, fluorometholone, fluocinolone acetonide, prednisone, prednisolone, methylprednisone, corticol, cortisone, fluocortisone, deoxycorticosterone acetate, aldosterone, and budesonide.

12. The pharmaceutical composition of claim 1, further comprising at least one antioxidant selected from the group consisting of ascorbic acid, erythorbic acid, sodium ascorbate, thioglycerol, cysteine, acetylcysteine, cystine, dithioerythreitol, dithiothreitol, glutathione, tocopherols, butylated hydroxyanisol, butylated hydroxytoluene, sodium sulfate, sodium bisulfite, acetone sodium bisulfite, sodium metabisulfite, sodium sulfite, sodium formaldehyde sulfoxylate, sodium thiosulfate, and nordihydroguaiaretic acid.

13. The pharmaceutical composition of claim 1, wherein the mycophenolic acid is present at a concentration of 0.05% w/w to 0.3% w/w.

14. The pharmaceutical composition of claim 13, wherein the first component includes mycophenolic acid at a concentration of about 0.1%, about 0.2%, or about 0.3% w/w and betamethasone at a concentration of about 0.01%, about 0.02%, or about 0.03% w/w.

15. The pharmaceutical composition of claim 1, wherein the concentration of the betamethasone is about 0.05% w/w.

16. The pharmaceutical composition of claim 1, further comprising at least one excipient or surfactant selected from the group consisting of a non-ionic polyoxyethlene-polyoxypropylene block copolymer, methylcellulose, a hydroxypropyl methylcellulose polymer, a polycarbophil polymer, edetate disodium dihydrate (EDTA), polysorbate-80, sodium thiosulfate, sodium thiosulfate pentahydrate, sodium phosphate, sodium phosphate dibasic anhydrous, and sodium phosphate monobasic anhydrous.

17. The pharmaceutical composition of claim 16, wherein the concentration of the excipient or surfactant is between about 0.1% w/w and 4.0% w/w.

18. A method for treating, preventing, and/or alleviating an ocular surface disease in a mammalian subject in need thereof comprising administering to the subject a therapeutically effective amount of the composition of claim 1.

19. The method of claim 18, wherein the administration is by topical drops or direct injection into the eye of the subject.

20. The method of claim 18, wherein the ocular surface disease is selected from the group consisting of keratoconjunctivitis sicca, episodic dry eye disease, recalcitrant dry eye disease, age-related dry eye, neurotrophic ocular surface disease, meibomian gland disease, and blepharitis.

21. The method of claim 20, wherein the ocular surface disease is keratoconjunctivitis sicca.

22. A method for treating, preventing, and/or alleviating an ocular surface disease in a mammalian subject in need thereof comprising administering to the subject a therapeutically effective amount of the composition of claim 8.

23. The pharmaceutical composition of claim 1, wherein the betamethasone is at a concentration of about 0.01%.

* * * * *